(12) United States Patent
Park et al.

(10) Patent No.: US 11,345,655 B2
(45) Date of Patent: May 31, 2022

(54) PSEUDOCERAMIDE COMPOUND AND SKIN EXTERNAL COMPOSITION COMPRISING THE SAME

(71) Applicant: NEOPHARM CO., LTD., Daejeon (KR)

(72) Inventors: Bu-Mahn Park, Daejeon (KR); Hye Seong Shin, Daejeon (KR)

(73) Assignee: NEOPHARM CO., LTD., Daejeon (KR)

( * ) Notice: Subject to any disclaimer, the term of this patent is extended or adjusted under 35 U.S.C. 154(b) by 227 days.

(21) Appl. No.: 16/653,464

(22) Filed: Oct. 15, 2019

(65) Prior Publication Data
US 2020/0115323 A1 Apr. 16, 2020

(30) Foreign Application Priority Data
Oct. 16, 2018 (KR) .......................... 10-2018-0123127

(51) Int. Cl.
| | | |
|---|---|---|
| *C07C 233/18* | (2006.01) | |
| *C07C 233/20* | (2006.01) | |
| *A61P 17/08* | (2006.01) | |
| *A61Q 19/00* | (2006.01) | |
| *A61K 8/42* | (2006.01) | |

(52) U.S. Cl.
CPC ............. *C07C 233/18* (2013.01); *A61K 8/42* (2013.01); *A61P 17/08* (2018.01); *A61Q 19/007* (2013.01); *C07C 233/20* (2013.01)

(58) Field of Classification Search
None
See application file for complete search history.

(56) References Cited

FOREIGN PATENT DOCUMENTS

| | | |
|---|---|---|
| EP | 0227994 B1 | 9/1989 |
| EP | 0097059 B1 | 10/1989 |
| EP | 0282816 B1 | 9/1993 |
| KR | 100236304 B1 | 7/1997 |
| KR | 100245797 B1 | 12/1997 |
| KR | 1998034991 A | 8/1998 |
| KR | 10-2017-0103359 A * | 3/2016 |

OTHER PUBLICATIONS

CAPLUS 2017-1506809.*
KR10-2017-0103359 machine translation.*
Walter M. Holleran, et al., entitled, "Sphingolipids Are Required for Mammalian Epidermal Barrier Function Inhibition of Sphingolipid Synthesis Delays Barrier Recovery After Acute Perturbation," The Journal of Clinical Investigation, Inc., vol. 88, Oct. 1991, pp. 1338-1345.
Genji Imokawa, et al., entitled, "Decreased Level of Ceramides in Stratum Corneum of Atopic Dermatitis: An Etiologic Factor in Atopic Dry Skin?" The Society for Investigative Dermatology, Inc., Apr. 1991, pp. 523-526.

* cited by examiner

*Primary Examiner* — Heidi Reese
(74) *Attorney, Agent, or Firm* — Nixon Peabody LLP; Thomas P. Pavelko

(57) ABSTRACT

Provided are a novel pseudoceramide compound and a skin external composition comprising the same. The skin external composition comprising a pseudoceramide compound or a pharmaceutically acceptable salt or solvate thereof according to the present invention as an active ingredient has an excellent effect of improving a skin barrier function, thereby exhibiting an effect of improving inflammatory skin diseases, and also is excellent in the function of improving the skin barrier and the effect of enhancing skin moisture.

11 Claims, 1 Drawing Sheet

PSEUDOCERAMIDE COMPOUND AND SKIN EXTERNAL COMPOSITION COMPRISING THE SAME

CROSS-REFERENCE TO RELATED APPLICATIONS

This application claims priority under 35 U.S.C. § 119 to Korean Patent Application No. 10-2018-0123127, filed on Oct. 16, 2018, in the Korean Intellectual Property Office, the disclosure of which is incorporated herein by reference in its entirety.

TECHNICAL FIELD

The following disclosure relates to a novel pseudoceramide compound having similar characteristics to skin protection, moisture retention, or the like of natural ceramides, and a use thereof.

BACKGROUND

Human skin acts as a barrier to physical and chemical stimuli from the external environment. However, in the skin of patients with inflammatory skin diseases such as atopic dermatitis, it can be seen that skin barrier function and/or water retention function in a stratum corneum is significantly reduced compared to normal skin, and the cause of such dysfunction has been found to be due to a reduction of ceramide in the skin (Non-Patent Document 1).

Ceramide, one of sphingolipids, has a structure in which fatty acids are linked to sphingosine, and accounts for 40-50% of intercorneocyte lipids that make up the skin stratum corneum. The skin stratum corneum acts as a protective barrier that protects against penetration of harmful substances or microorganisms from the external environment into the skin tissue. At this time, ceramide forms a layered structure of the skin stratum corneum, and thus has been known to play a central role in maintaining moisture and barrier, which are basic functions of the skin. In maintaining the basic functions of the skin normally, the significance of ceramide has also been proved for a necessity by experimental results that only when the ceramide biosynthesis is inhibited or when the ceramide content is decreased, the barrier function of the skin is not restored, the moisture evaporation of the skin is increased, and various skin diseases are worsened (Non-Patent Document 2). In addition, when the aging of the skin is progressed or the ceramide content is reduced by external stimulation, it has been known that the skin may be restored to be normal by supplementing ceramides.

For the purpose of supplementing such ceramides, searches have been made for natural animals and plants, and microbial systems, and it has been known that the ceramides may be extracted from various animals, plants, and microorganisms (yeasts) containing ceramides. However, the ceramides are present in extremely small amounts in these animals plants, and microorganisms, and the cost of their extract production is too expensive, and solubility in various solvents, cosmetics, and raw materials used in cleaning products is very low. Thus, the synthesis of ceramides with the same structure as natural ceramides or pseudoceramides with similar structures to natural ceramides has been studied by many scientists. Examples thereof include Japanese Patent Documents 1 and 2 of Huawang Co., Ltd. of Japan, and Patent Document 3 of Unilever Co., Ltd. of Germany and Patent Documents 4 and 5 of AMOREPACIFIC, and Patent Document 6 of Aekyung Industrial Co., Ltd. in Korea.

The applicant has made intensified studies of pseudoceramides to find novel pseudoceramide compounds with structural characteristics similar to natural ceramide I and excellent effects of skin protection, moisture retention, or the like, thereby completing the present invention.

RELATED ART DOCUMENT

Patent Document (Patent Document 1) EP 0227994 B1
(Patent Document 2) EP 0282816 B1
(Patent Document 3) EP 0097059 B1
(Patent Document 4) KR 10-0236304 B1
(Patent Document 5) KR 10-0245797 B1
(Patent Document 6) KR 10-1998-0034991 A

Non-Patent Document (Non-Patent Document 1) Imokawa G et al., Decreased level of ceramides in stratum corneum of atopic dermatitis: An etiologic factor on atopic dry skin, J Invest Dermatol., 96, pp. 523-526, 1991
(Non-Patent Document 2) Holleran W M et al., Sphingolipids are required for mammalian epidermal barrier function. Inhibition of sphingolipid synthesis delays barrier recovery after acute perturbation., J Clin Invest, 88, pp. 1338-1345, 1991

SUMMARY

An embodiment of the present invention is directed to providing a novel pseudoceramide compound of natural ceramide type I or a pharmaceutically acceptable salt or solvate thereof, which has characteristics similar to those of the natural ceramides for skin protection, moisture retention, or the like.

Another embodiment of the present invention is directed to providing a pharmaceutical composition for improving a skin barrier function and improving inflammatory skin disease, comprising a novel pseudoceramide compound or a pharmaceutically acceptable salt or solvate thereof according to the present invention as an active ingredient.

Another embodiment of the present invention is directed to providing a cosmetic composition for improving a skin barrier function and enhancing skin moisture, comprising a novel pseudoceramide compound or a pharmaceutically acceptable salt or solvate thereof according to the present invention as an active ingredient.

In one general aspect, there is provided a pseudoceramide compound represented by the following Formula 1:

[Formula 1]

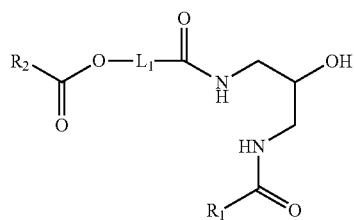

wherein

R₁ is (C1-C30) alkyl, (C2-C30) alkenyl, or (C2-C30) alkynyl;

R₂ is (C1-C30) alkyl or (C2-C30) alkenyl; and

L₁ is (C1-C30) alkylene, (C2-C30) alkenylene, or (C2-C30) alkynylene;

or a pharmaceutically acceptable salt or solvate thereof.

In Formula 1, R₁ may be (C1-C30) alkyl or (C2-C30) alkenyl, R₂ may be linear (C1-C30) alkyl, and L₁ may be (C2-C30) alkylene.

In Formula 1, R₁ may be (C7-C30) alkyl or (C7-C30) alkenyl, R₂ may be linear (C7-C30) alkyl, and L₁ may be (C7-C30) alkylene.

In another general aspect, there is provided a pharmaceutical composition for improving a skin barrier function and improving inflammatory skin diseases, comprising a novel pseudoceramide compound represented by Formula 1, a pharmaceutically acceptable salt or solvate thereof as an active ingredient.

The inflammatory skin disease may be atopic dermatitis, psoriasis, contact dermatitis, eczema dermatitis, photodermatitis, seborrheic dermatitis, herpes dermatitis, lichen planus, lichen sclerosus, pyoderma gangrenosum, pemphigus, epidermolysis bullosa, or systemic sclerosis.

The pharmaceutical composition may comprise an active ingredient in an amount of 0.001 to 20 wt %, based on the total weight of the composition.

In another general aspect, there is provided a cosmetic composition for improving a skin barrier function and enhancing skin moisture, comprising a pseudoceramide compound represented by Formula 1 or a pharmaceutically acceptable salt or solvate thereof as an active ingredient.

The cosmetic composition may further comprise intercorneocyte lipids or lipid complexes similar thereto.

In the cosmetic composition, the intercorneocyte lipids or lipid complexes similar thereto may be one or two or more selected from cholesterol, phytosterol, sphingosine, phytosphingosine, and cerebroside; ceramide I; ceramide II; ceramide III; ceramide IIIB; ceramide IV; ceramide V; and ceramide VI, myristoyl/palmitoyl oxostearamide/arachamide MEA, and dihydroxyisopropyl palmoyl palmamide.

The cosmetic composition may include an active ingredient in an amount of 0.001 to 20 wt %, based on the total weight of the composition.

Other features and aspects will be apparent from the following detailed description, the drawings, and the claims.

DETAILED DESCRIPTION OF EMBODIMENTS

Figure 1:
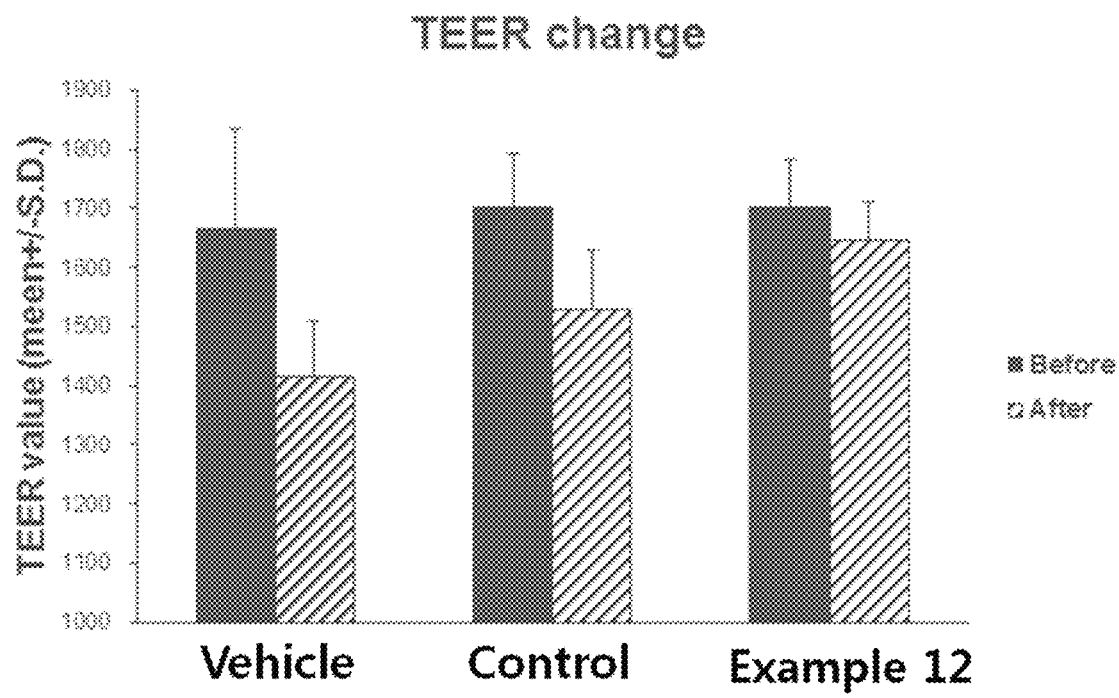
FIG. 1 is results of transepithelial electrical resistance (TEER) obtained by evaluating artificial skin integrity according to an embodiment of the present invention.

Hereinafter, a pseudoceramide compound according to the present invention and a use thereof will be described in detail below. However, unless otherwise indicated, technical terms and scientific terms used herein have the general meaning understood by those skilled in the art to which the present invention pertains and a description for the known function and configuration unnecessarily obscuring the gist of the present invention will be omitted in the following description.

The terms used herein are defined as follows.

As used herein, the term "evaluation of artificial skin integrity" refers to a method of evaluating a degree of improvement of the skin barrier by measuring the electrical resistance of artificial skin.

In addition, as used herein, the term "pharmaceutically acceptable salt" refers to a salt or a complex that retains a desired biological activity of the pseudoceramide compound according to the invention, but exhibits minimal or no undesirable toxic effects. Specifically, the pharmaceutically acceptable salt may be, but is not limited thereto, acid addition salts formed of an inorganic acid such as hydrochloric acid, hydrobromic acid, sulfuric acid, nitric acid, phosphoric acid, or the like; or an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid, and muconic acid.

In addition, as used herein, the term "solvate" refers to a higher order of compound produced between molecules or ions of a solute and molecules or ions of a solvent, and a hydrate to which water is bound is also included here.

Unless otherwise dictated below, the term "pseudoceramide compound according to the present invention" or "compound of Formula 1" may be the compound itself, a pharmaceutically acceptable salt, a solvate, or the like, and of course, may be used as a concept that includes all isomers and prodrugs thereof.

In addition, as used herein, the term "alkyl" refers to an organic radical derived from a hydrocarbon in a linear or branched form.

In addition, as used herein, the term "alkenyl" refers to an organic radical derived from a linear or branched hydrocarbon containing one or more double bonds.

In addition, the term "alkynyl" used herein refers to an organic radical derived from a linear or branched hydrocarbon containing one or more triple bonds.

The present inventors have been studying new formulations for optimizing the protective function of the skin, and found a novel pseudoceramide compound with a structure of natural ceramide type I. The pseudoceramide compound according to the present invention acts as a constituent of intercorneocyte lipids to implement an excellent effect on improving a skin barrier function.

In addition, a pseudoceramide compound according to the present invention is combined with components such as fatty acids and intercorneocyte lipids to form a sheet-like arrangement that forms an orderly and dense structure of the epidermal layer of the skin and promote differentiation of keratinocyte.

Hereinafter, a pseudoceramide compound or a pharmaceutically acceptable salt or solvate thereof according to the present invention will be described.

A pseudoceramide compound according to an exemplary embodiment of the present invention may be represented by the following Formula 1. In addition, a pharmaceutically acceptable salt or solvate of the pseudoceramide compound may also be an aspect of the present invention:

[Formula 1]

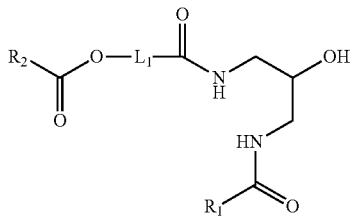

wherein $R_1$ is (C1-C30) alkyl, (C2-C30) alkenyl, or (C2-C30) alkynyl;

$R_2$ is (C1-C30) alkyl or (C2-C30) alkenyl; and $L_1$ is (C1-C30) alkylene, (C2-C30) alkenylene, or (C2-C30) alkynylene.

The pseudoceramide compound may have an asymmetric structure. Due to this structural feature, compatibility and affinity for an intercellular lipid lamellar layer are so excellent that it is not only easily absorbed in the stratum corneum, but also more stably located on the intercellular lipid lamellar layer.

A pseudoceramide compound according to an exemplary embodiment of the present invention may be represented by the following Formula 2:

[Formula 2]

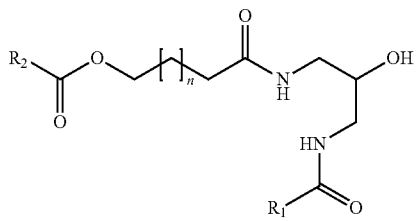

wherein $R_1$ is (C1-C30) alkyl, (C2-C30) alkenyl, or (C2-C30) alkynyl;

$R_2$ is (C1-C30)alkyl; and n is an integer of 0 to 28.

In terms of that high moisture retention effects with an enhancement of more enhanced skin barrier function may be embodied, the pseudoceramide compound according to an exemplary embodiment of the present invention may be specifically a pseudoceramide compound in which in Formula 1, $R_1$ is (C1-C30) alkyl or (C2-C30) alkenyl, $R_2$ is linear (C1-C30) alkyl, and $L_1$ is (C2-C30) alkylene.

More specifically, in Formula 1, $R_1$ may be (C7-C30) alkyl or (C7-C30) alkenyl, $R_2$ may be linear (C7-C30) alkyl, and $L_1$ may be (C7-C30) alkylene.

As mentioned above, the pseudoceramide compound according to the present invention has an asymmetric structure, and the substituents included in the amide group present in the molecule preferably have a different carbon number.

For example, $R_1$ of Formula 1 and

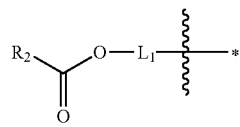

(hereinafter, referred to as substituent A) may have different carbon numbers from each other.

For example, the total carbon number of $R_1$ of Formula 1 may be smaller than the total carbon number of substituent A, and the difference in the total carbon number thereof may be 1 to 25.

Most preferably, the pseudoceramide compound according to an exemplary embodiment of the present invention may be at least one selected from the following structures, but is not limited thereto.

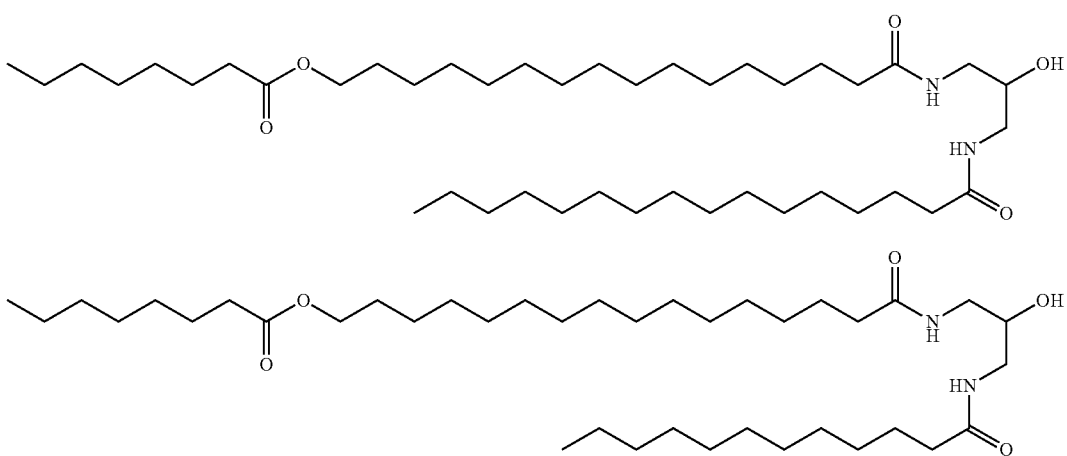

-continued
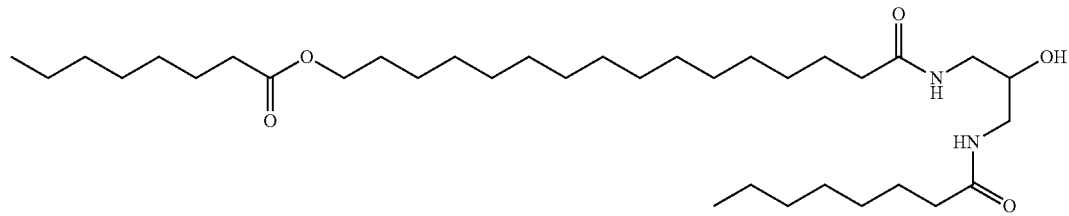
3
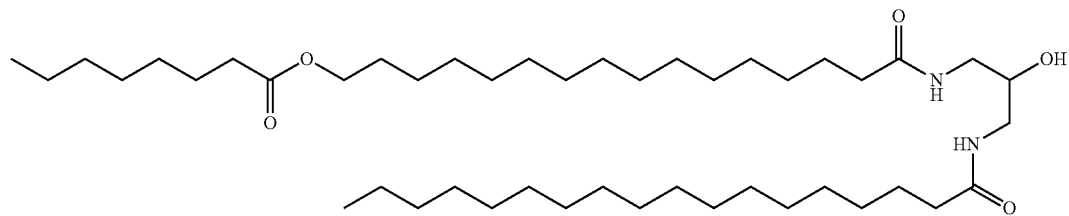
4
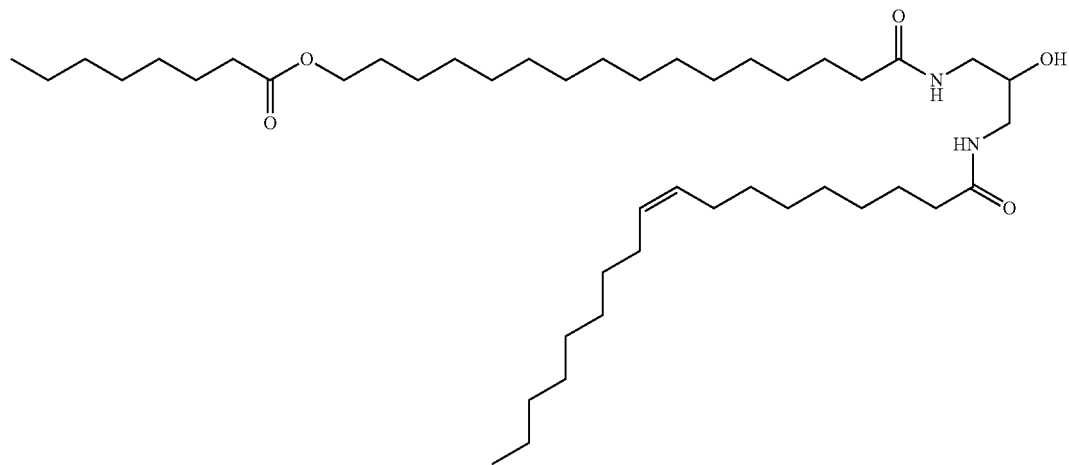
5
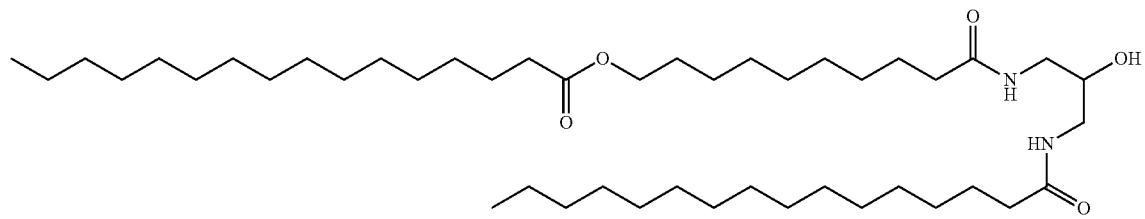
6
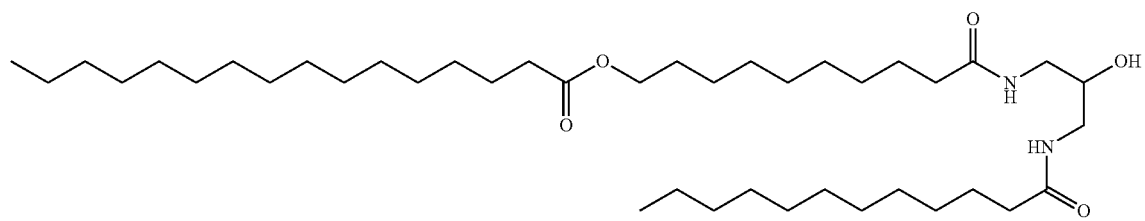
7
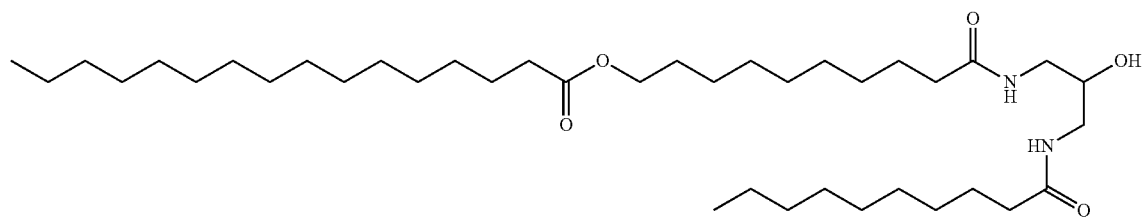
8

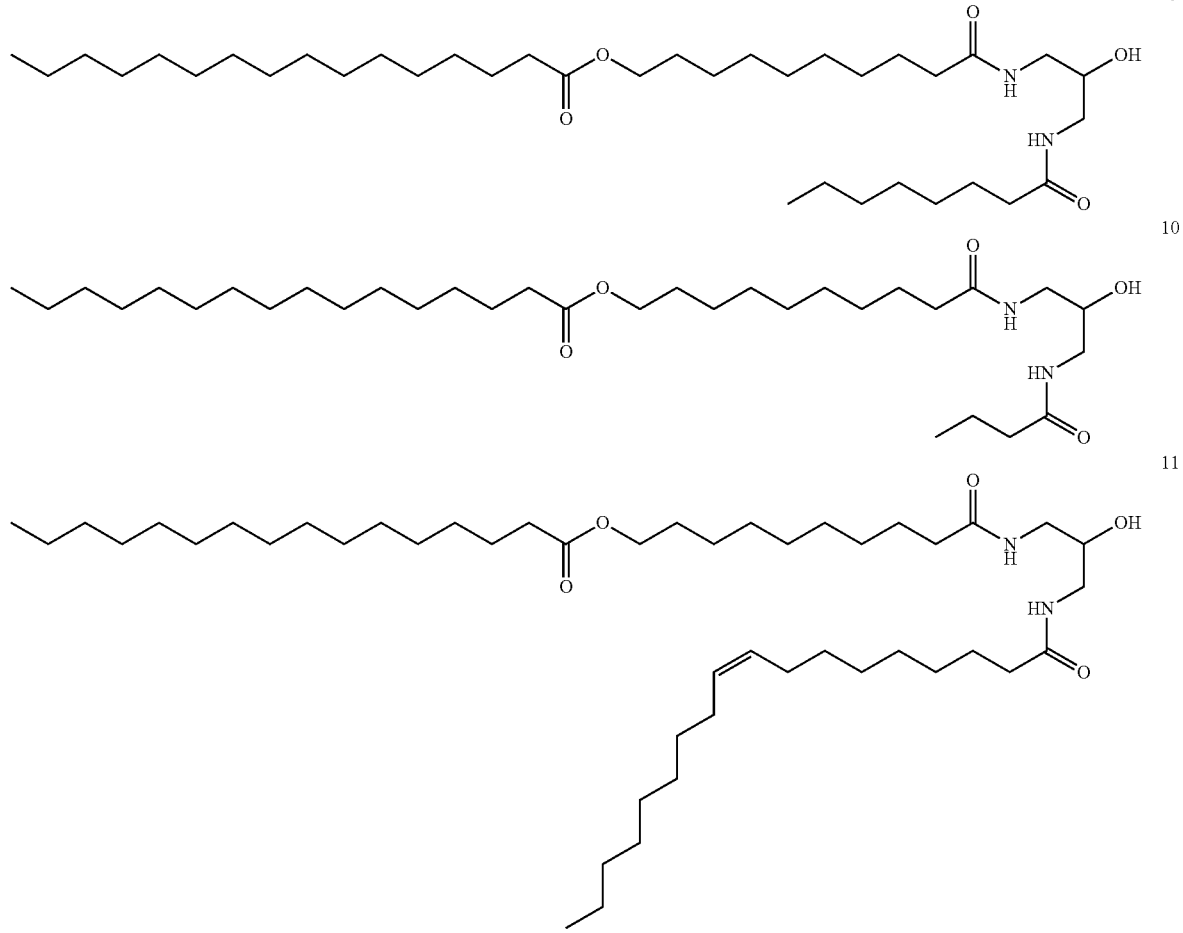

Hereinafter, the use of the pseudoceramide compound or a pharmaceutically acceptable salt or solvate thereof according to the present invention will be described.

The pseudoceramide compound or a pharmaceutically acceptable salt or solvate thereof according to the present invention as described above may exhibit strong affinity to the skin surface and the stratum corneum which is the outer layer of the skin when applied to the skin, and compact their structures to optimize water retention function, and at the same time may be used as an active ingredient of a composition for improving dry skin or keeping skin healthy.

In an aspect, the composition may be a pharmaceutical composition for improving a skin barrier function. In an aspect, the composition may be a pharmaceutical composition for improving and treating an inflammatory skin disease.

In an aspect, the composition may be a cosmetic composition for improving a skin barrier function.

In an aspect, the composition may be a cosmetic composition for enhancing skin moisture.

Specifically, the cosmetic composition according to an exemplary embodiment of the present invention may be a cosmetic composition comprising a pseudoceramide compound represented by Formula 1 or a pharmaceutically acceptable salt or solvate thereof as an active ingredient.

The cosmetic composition according to an exemplary embodiment of the present invention restores the skin barrier function, thereby improving skin problems such as drying or roughening of the skin. In addition, the cosmetic composition effectively increases the expression of involucrin or flaggrin which is a peptide constituting the skin barrier, and thereby is effective in improving and preventing skin diseases that may occur due to the damage of skin barrier as well as the above-described skin problems.

That is, according to the present invention, the upper layer of the epidermis, which is the outermost layer of the skin, effectively recovers the stratum corneum consisting of keratinocytes, and is the most important first line of defense against toxic substances, microorganisms, mechanical stimuli, and ultraviolet rays, and functions to provide an environment which may perform the skin's ability for normal function by inhibiting a loss of electrolytes or moisture through the skin. In addition, according to the present invention, components such as fatty acids, intercorneocyte lipids, or the like are combined to intensify the moisturizing effect of the skin with a stable and regular arrangement to form an orderly and dense layer of the epidermal layer of the skin.

The cosmetic composition according to an exemplary embodiment of the present invention may further comprise intercorneocyte lipids or lipid complexes similar thereto, in addition to the compound represented by Formula 1.

As an example, the intercorneocyte lipids or lipid complexes similar thereto are not limited as long as it is a lipid component that may be used in a cosmetic composition. However, specific examples thereof include one or a mixture of two more selected from cholesterol, phytosterol, sphingosine, phytosphingosine, and cerebroside; ceramide I; ceramide II; ceramide III; ceramide IIIB; ceramide IV; ceramide V; and ceramide VI, myristoyl/palmitoyl oxostearamide/arachamide MEA, and dihydroxyisopropyl palmoyl palmamide, or the like.

As an example, the lipid component may be included in an amount of 0.01 to 10 wt %, specifically 0.01 to 5 wt %, and more specifically 0.01 to 1 wt %, based on the total weight of the cosmetic composition.

In addition, the cosmetic composition according to an exemplary embodiment of the present invention may include the effective ingredients in an amount of 0.001 to 20 wt %, specifically 0.001 to 10 wt %, and more specifically 0.001 to 3 wt %, based on the total weight of the cosmetic composition.

In addition, in the cosmetic composition according to an embodiment of the present invention, the above-described lipid component may be used in an amount of 1 to 100 parts by weight, based on 100 parts by weight of the active ingredient. Specifically, the intercorneocyte lipids or lipid complexes similar thereto may be used in an amount of 1 to 50 parts by weight, and more specifically 1 to 10 parts by weight, based on 100 parts by weight of the active ingredient.

The cosmetic composition according to an exemplary embodiment of the present invention is not particularly limited in formulation and may be appropriately selected as desired.

As an example, the cosmetic composition may be formulated into a formulation selected from the group consisting of softening cream, converging cream, nutrient cream, eye cream, nutrition cream, massage cream, cleansing cream, cleansing foam, cleansing water, powder, essence, pack, or the like.

In addition, the cosmetic composition may further comprise additional additives as appropriate. As an example of the additives, one or more aqueous additives selected from stabilizers, emulsifiers, thickeners, moisturizers, liquid crystal film strengthening agents, pH regulators, antibacterial agents, water-soluble polymers, coating agents, metal-ion sequestrants, amino acids, organic amines, polymer emulsions, pH adjusters, skin nutrients, antioxidants, antioxidant aids, preservatives, fragrances, or the like; and at least one oily additives selected from fats and oils, waxes, hydrocarbon oils, higher fatty acid oils, higher alcohols, synthetic ester oils, and silicone oils may be mentioned.

Here, each of the additives may be included in 0.001 to 20 wt %, specifically 0.01 to 10 wt %, and more specifically 0.05 to 10 wt %, based on the total weight of the composition, but is not limited thereto.

Specifically, the pharmaceutical composition according to an exemplary embodiment of the present invention may be a pharmaceutical composition comprising a pseudoceramide compound represented by Formula 1 or a pharmaceutically acceptable salt or solvate thereof as an active ingredient.

The pharmaceutical composition according to the present invention significantly increases the expression of involucrin, which is a peptide constituting the skin barrier upon treatment to keratinocytes, and shows excellent skin barrier function improvement and strengthening. Furthermore, the pharmaceutical composition shows an excellent effect on the improvement and treatment of inflammatory skin diseases caused by skin barrier damage.

The inflammatory skin diseases may be atopic dermatitis, psoriasis, contact dermatitis, eczema dermatitis, photodermatitis, seborrheic dermatitis, herpes dermatitis, lichen planus, lichen sclerosus, pyoderma gangrenosum, pemphigus, epidermolysis bullosa, systemic sclerosis, or the like, and in particular, it is useful in preventing, improving or treating chronic skin diseases such as atopic dermatitis, psoriasis, and contact dermatitis.

In addition, the pharmaceutical composition according to an exemplary embodiment of the present invention may include an effective ingredient in an amount of 0.001 to 20 wt %, specifically 0.001 to 10 wt %, and more specifically 0.001 to 3 wt %, based on the total weight of the pharmaceutical composition.

The pharmaceutical composition according to an embodiment of the present invention is not particularly limited in formulation, and may be appropriately selected as desired.

As an example, the pharmaceutical composition may be formulated into a skin external formulation selected from the group consisting of lotions, ointments, gels, creams, patches, sprays, or the like.

In addition, the pharmaceutical composition may appropriately include additional pharmaceutically acceptable carriers as desired. Examples thereof include, but is not limited thereto, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate or mineral oil. In addition, the pharmaceutical composition may further include a carrier such as a lubricant, a humectant, a sweetener, a flavoring agent, an emulsifier, a suspending agent, or a preservative, in addition to the above-described carriers.

Here, each of the carriers may be included in an amount of 0.001 to 20 wt %, specifically, 0.01 to 10 wt %, and more specifically, 0.05 to 10 wt %, based on the total weight of the composition, but is not limited thereto.

Hereinafter, preferred examples are provided to aid in understanding the present invention. However, the following examples are provided only to make the present invention easier to understand, and the following examples are merely exemplary and are not intended to limit the scope of the present invention in any way.

Example 1

Preparation of Pseudoceramide Compound (1)

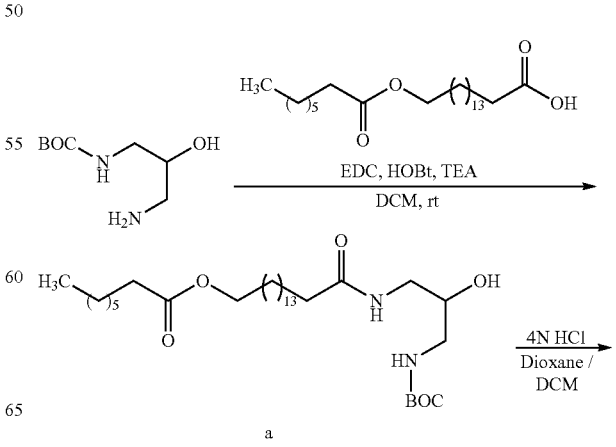

a

-continued

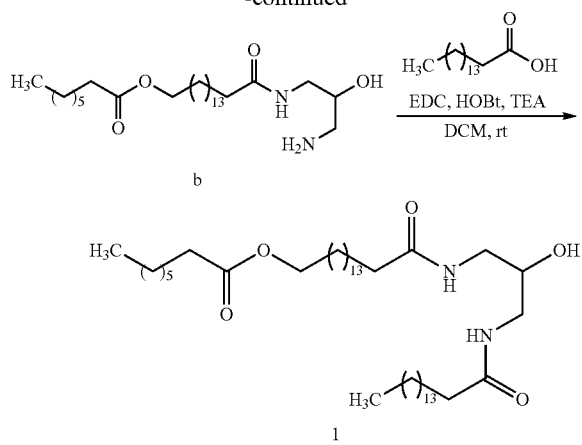

Step 1. Preparation of 16-((3-(((tert-butoxycarbonyl)amino)-2-hydroxypropyl)amino)-16-oxohexadecyl Octanoate (Compound a)

Dichloromethane (DCM, 30 mL, Samjeon Pure Chemical) and triethylamine (TEA, 1.47 mL, Samjeon Pure Chemical) were added to tert-butyl (3-amino-2-hydroxypropyl)carbamate (1.00 g, 5.26 mmol) to form a reaction solution. After 10 minutes at room temperature (25° C.), a solution of EDC.HCl (1.51 g, 7.89 mmol, Sigma-Aldrich), HOBt (1.07 g, 7.89 mmol, Sigma-Aldrich), and 16-(octanoyloxy)hexadecanoic acid (2.10 g, 5.26 mmol) dissolved in dichloromethane (DCM, 33 mL) was slowly added to the reaction solution, followed by stirring at room temperature for 12 hours. After stirring, 90 mL of dichloromethane, 90 mL of water, and 8 mL of ethanol were added to the reaction solution, the resulting mixture was stirred and left to separate into layers. The organic layer was dried over anhydrous Na$_2$SO$_4$ and filtered, and then the filtrate was concentrated under reduced pressure. The residue was separated by column chromatography (dichloromethane: methanol=40:1) to obtain a compound a (1.27 g, yield: 42%) as a white solid.

MS (ESI pos. ion) m/z: 571 (MH+). 1H NMR (600 MHz, CDCl3): 6.31 (brs, 1H), 5.12 (brs, 1H), 4.06 (t, J=6.6 Hz, 2H), 3.92 (brs, 1H), 3.76-3.74 (m, 1H), 3.45-3.41 (m, 1H), 3.31-3.22 (m, 2H), 3.18-3.13 (m, 1H), 2.29 (t, J=7.8 Hz, 2H), 2.22 (t, J=7.8 Hz, 2H), 1.66-1.59 (m, 8H), 1.44 (s, 9H), 1.34-1.25 (m, 28H), 0.88 (t, J=7.2 Hz, 2H).

Step 2. Preparation of 16-((3-(12-azaneyl)-2-hydroxypropyl)amino)-16-oxohexadecyl Octanoate (Compound b)

Dichloromethane (DCM, 6 mL, Samjeon Pure Chemical) was added to compound a (1.54 g, 2.70 mmol) to prepare a reaction solution. After cooling the reaction solution to 0° C., a solution of 4N hydrochloric acid (4N HCl in dioxane, 4.62 mL, Sigma-Aldrich) dissolved in 1,4-dioxane was slowly added to the reaction solution and stirred for 12 hours at room temperature. After stirring, 95 mL of dichloromethane, 95 mL of water, and 5 mL of methanol were added to the reaction solution. The mixture was adjusted to pH=9 with a concentrated aqueous sodium hydroxide solution, and stirred and left to separate into layers. The organic layer was concentrated under reduced pressure to obtain a compound b (1.27 g, yield: 100%) as a white solid, and then proceeded to next steps without further purification.

Step 3. Preparation of Pseudoceramide Compound (1)

Dichloromethane (DCM, 8 mL, Samjeon Pure Chemical) and triethylamine (TEA, 0.25 mL, Samjeon Pure Chemical) were added to compound b (0.42 g, 0.90 mmol) to prepare a reaction solution. After 5 minutes at room temperature, a solution of EDC.HCl (0.26 g, 1.35 mmol, Sigma-Aldrich), HOBt (0.18 g, 1.35 mmol, Sigma-Aldrich), and palmitic acid (0.23 g, 0.90 mmol, Sigma-Aldrich) dissolved in dichloromethane (DCM, 4 mL) was slowly added to the reaction solution, followed by stirring at room temperature for 12 hours. After stirring, 52 mL of dichloromethane, 52 mL of water, and 13 mL of ethanol were added to the reaction solution, the resulting mixture was stirred and left to separate into layers. The organic layers were collected and concentrated under reduced pressure, and the residue was separated by column chromatography (dichloromethane: methanol=50:1) to obtain compound 1 (0.223 g, yield: 35%) as a white solid.

The obtained products were analyzed by MS (Agilent, USA) and NMR (Varian, USA), and the results are shown in Table 1 below.

Examples 2 to 11

Preparation of Pseudoceramide Compound

Using similar methods to that of Example 1, pseudoceramide compounds 2 to 11 having the structures shown in Table 1 were prepared.

The obtained products were analyzed by MS (Agilent, USA) and NMR (Varian, USA), and the results are shown in Table 1 below.

TABLE 1

| Examples | Structure of the compound | MS and NMR data |
|---|---|---|
| 1 | | MS (ESI pos. ion) m/z: 710 (MH+). 1H NMR (600 MHz, CDCl3): 6.26-6.25 (m, 2H), 4.06 (t, J = 7.2 Hz, 3H), 3.76-3.74 (m, 1H), 3.43-3.38 (m, 2H), 3.28-3.24 (m, 2H), 2.29 (t, J = 7.8 Hz, 2H), 2.22 (t, J = 7.8 Hz, 4H), 1.65-1.58 (m, 10H), 1.31-1.25 (m, 52H), 0.88 (t, J = 7.2 Hz, 6H). |

TABLE 1-continued

| Examples | Structure of the compound | MS and NMR data |
|---|---|---|
| 2 | H$_3$C-(　)$_5$-C(O)-O-(　)$_{13}$-C(O)-NH-CH$_2$-CH(OH)-CH$_2$-NH-C(O)-(　)$_5$-CH$_3$; other chain H$_3$C-(　)$_9$-C(O)- | MS (ESI pos. ion) m/z: 654 (MH+). 1H NMR (600 MHz, CDCl3): 6.23-6.19 (m, 2H), 4.06 (t, J = 7.2 Hz, 2H), 3.98 (t, J = 3.6 Hz, 1H), 3.77-3.74 (m, 1H), 3.44-3.39 (m, 2H), 3.27-3.22 (m, 2H), 2.29 (t, J = 7.8 Hz, 2H), 2.22 (t, J = 7.8 Hz, 4H), 1.66-1.50 (m, 10H), 1.30-1.25 (m, 44H), 0.88 (t, J = 7.2 Hz, 6H). |
| 3 | H$_3$C-(　)$_5$-C(O)-O-(　)$_{13}$-C(O)-NH-CH$_2$-CH(OH)-CH$_2$-NH-C(O)-(　)$_5$-CH$_3$ | MS (ESI pos. ion) m/z: 597 (MH+). 1H NMR (600 MHz, CDCl3): 6.22-6.18 (m, 2H), 4.05 (t, J = 7.2 Hz, 2H), 3.98-3.96 (m, 1H), 3.75 (q, J = 4.8 Hz, 1H), 3.45-3.40 (m, 2H), 3.26-3.22 (m, 2H), 2.29 (t, J = 7.8 Hz, 2H), 2.22 (t, J = 7.8 Hz, 4H), 1.62-1.58 (m, 10H), 1.31-1.25 (m, 36H), 0.88 (t, J = 7.2 Hz, 6H). |
| 4 | H$_3$C-(　)$_5$-C(O)-O-(　)$_{13}$-C(O)-NH-CH$_2$-CH(OH)-CH$_2$-NH-C(O)-(　)$_{15}$-CH$_3$ | MS (ESI pos. ion) m/z: 738 (MH+). 1H NMR (600 MHz, CDCl3): 6.39-6.36 (m, 2H), 4.05 (t, J = 7.2 Hz, 3H), 3.78-3.74 (m, 1H), 3.39-3.34 (m, 2H), 3.30-3.26 (m, 2H), 2.29 (t, J = 7.8 Hz, 2H), 2.22 (t, J = 7.8 Hz, 4H), 1.63-1.58 (m, 10H), 1.29-1.24 (m, 56H), 0.88 (t, J = 7.2 Hz, 6H). |
| 5 | H$_3$C-(　)$_5$-C(O)-O-(　)$_{13}$-C(O)-NH-CH$_2$-CH(OH)-CH$_2$-NH-C(O)-(　)$_5$-CH=CH-(　)$_7$-CH$_3$ | MS (ESI pos. ion) m/z: 736 (MH+). 1H NMR (600 MHz, CDCl3): 6.22-6.21 (m, 2H), 5.36-5.32 (m, 2H), 4.05 (t, J = 7.2 Hz, 2H), 3.99 (t, J = 3.6 Hz, 1H), 3.77-3.74 (m, 1H), 3.45-3.40 (m, 2H), 3.27-3.22 (m, 2H), 2.29 (t, J = 7.8 Hz, 2H), 2.22 (t, J = 7.8 Hz, 4H), 2.04-1.99 (m, 4H), 1.63-1.58 (m, 10H), 1.30-1.25 (m, 48H), 0.88 (t, J = 7.2 Hz, 6H). |
| 6 | H$_3$C-(　)$_{13}$-C(O)-O-(　)$_7$-C(O)-NH-CH$_2$-CH(OH)-CH$_2$-NH-C(O)-(　)$_{13}$-CH$_3$ | MS (ESI pos. ion) m/z: 738 (MH+). 1H NMR (600 MHz, CDCl3): 6.26-6.23 (m, 2H), 4.05 (t, J = 7.2 Hz, 3H), 3.76 (br s, 1H), 3.43-3.38 (m, 2H), 3.28-3.24 (m, 2H), 2.29 (t, J = 7.8 Hz, 2H), 2.22 (t, J = 7.8 Hz, 4H), 1.64-1.58 (m, 10H), 1.30-1.25 (m, 56H), 0.88 (t, J = 7.2 Hz, 6H). |
| 7 | H$_3$C-(　)$_{13}$-C(O)-O-(　)$_7$-C(O)-NH-CH$_2$-CH(OH)-CH$_2$-NH-C(O)-(　)$_9$-CH$_3$ | MS (ESI pos. ion) m/z: 682 (MH+). 1H NMR (600 MHz, CDCl3): 6.27-6.25 (m, 2H), 4.05 (t, J = 7.2 Hz, 3H), 3.76 (br s, 1H), 3.41-3.38 (m, 2H), 3.29-3.25 (m, 2H), 2.29 (t, J = 7.8 Hz, 2H), 2.22 (t, J = 7.8 Hz, 4H), 1.63-1.59 (m, 10H), 1.30-1.25 (m, 48H), 0.88 (t, J = 7.2 Hz, 6H). |

TABLE 1-continued

| Examples | Structure of the compound | MS and NMR data |
|---|---|---|
| 8 | (structure) | MS (ESI pos. ion) m/z: 654 (MH+). 1H NMR (600 MHz, CDCl3): 6.26-6.24 (m, 2H), 4.06-4.02 (m, 3H), 3.76-3.75 (m, 1H), 3.42-3.39 (m, 2H), 3.27-3.25 (m, 2H), 2.29 (t, J = 7.8 Hz, 2H), 2.22 (t, J = 7.8 Hz, 4H), 1.63-1.60 (m, 10H), 1.30-1.25 (m, 44H), 0.88 (t, J = 7.2 Hz, 6H). |
| 9 | (structure) | MS (ESI pos. ion) m/z: 625 (MH+). 1H NMR (600 MHz, CDCl3): 6.25-6.23 (m, 2H), 4.06-4.02 (m, 3H), 3.77-3.74 (m, 1H), 3.43-3.38 (m, 2H), 3.28-3.24 (m, 2H), 2.29 (t, J = 7.8 Hz, 2H), 2.22 (t, J = 7.8 Hz, 4H), 1.64-1.57 (m, 10H), 1.31-1.25 (m, 40H), 0.88 (t, J = 7.2 Hz, 6H). |
| 10 | (structure) | MS (ESI pos. ion) m/z: 569 (MH+). 1H NMR (600 MHz, CDCl3): 6.25-6.24 (m, 2H), 4.06 (t, J = 7.2 Hz, 2H), 4.01 (d, J = 4.2 Hz, 1H), 3.77-3.76 (m, 1H), 3.44-3.39 (m, 2H), 3.29-3.25 (m, 2H), 2.29 (t, J = 7.8 Hz, 2H), 2.24-2.20 (m, 4H), 1.69-1.57 (m, 8H), 1.30-1.25 (m, 34H), 0.97 (t, J = 7.2 Hz, 3H), 0.89 (t, J = 7.2 Hz, 3H). |
| 11 | (structure) | MS (ESI pos. ion) m/z: 764 (MH+). 1H NMR (600 MHz, CDCl3): 6.31-6.27 (m, 2H), 5.37-5.31 (m, 2H), 4.12 (d, J = 4.2 Hz, 1H), 4.05 (t, J = 7.2 Hz, 2H), 3.77-3.74 (m, 1H), 3.40-3.36 (m, 2H), 3.30-3.26 (m, 2H), 2.29 (t, J = 7.8 Hz, 2H), 2.22 (t, J = 7.8 Hz, 4H), 2.02-1.99 (m, 4H), 1.64-1.58 (m, 10H), 1.30-1.23 (m, 52H), 0.88 (t, J = 7.2 Hz, 6H). |

Example 12

Preparation of Cosmetic Composition

The cosmetic compositions were prepared according to compositions of Table 2 below.

TABLE 2

| Raw material name | Example 12 | Comp. Example 1 | Negative control group |
|---|---|---|---|
| Myristoyl/palmitoyl oxostearamide/arachamide MEA | 1 | 1 | 1 |
| Sorbitan stearate | 5 | 5 | 5 |
| Stearic acid | 4.5 | 4.5 | 4.5 |
| Cetearyl alcohol | 10.5 | 10.5 | 10.5 |
| Carbomer | 0.1 | 0.1 | 0.1 |
| Example (compound 1) | 0.1 | — | — |
| Comparative Example (structure below) | — | 0.1 | — |
| Caprylic/Capric triglyceride | 15 | 15 | 15 |
| Glycerine | 10 | 10 | 10 |
| Purified water | Residual amount | Residual amount | Residual amount |

Comparative Example (structure below)

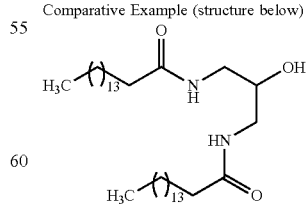

Figure 2:
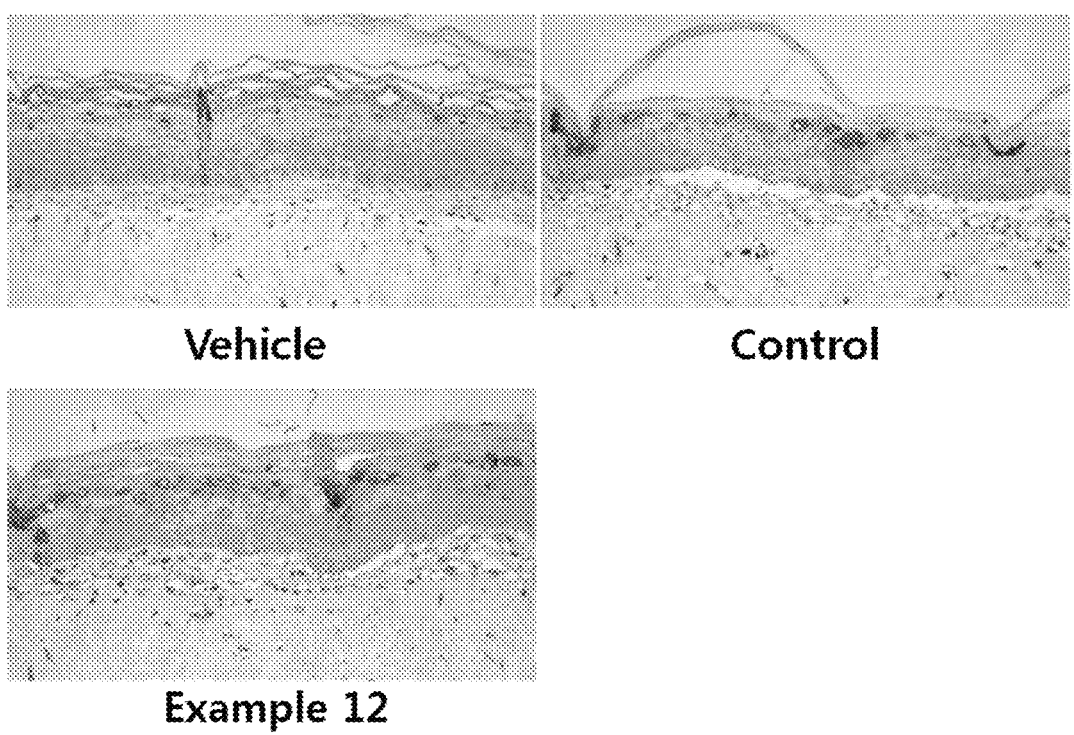
FIG. 2 is results of expression patterns of involucrin, which is a differentiation indicator protein, observed by an immunohistochemical stain in order to measure an effect of promoting differentiation of artificial skin according to an embodiment of the present invention.

Evaluation of the artificial skin integrity and measurement of an effect of promoting differentiation of artificial skin of the cosmetic composition were carried out by following methods, and the results are shown in FIGS. 1 and 2 below.

1. Evaluation of Artificial Skin Integrity

After applying each of the cosmetic compositions (about 500 mg) prepared from the composition of Table 2 to artificial skin (Keraskin™ from MCTT, Seoul, Korea), skin integrity before and 24 hours after application was evaluated through TEER (trans-epithelial electrical resistance) measurement. The results are shown in FIG. 1 below. At this time, in the following figures, the vehicle corresponds to the negative control group, and the control corresponds to Comparative Example 1.

As a result, in the case of the cosmetic composition (Example 12) containing Example 1, it could be confirmed as being effective to maintain skin integrity of 11.7% or more compared to the negative control group containing no compound of Examples and 6.8% or more compared to Comparative Example 1.

2. Measurement of Effect of Promoting Differentiation of Artificial Skin

After applying each of the cosmetic compositions (about 500 mg) prepared from the composition of Table 2 to artificial skin (Keraskin™ from MCTT, Seoul, Korea), the expression pattern of involucrin which is a differentiation indicator protein after 24 hours was observed by immunohistochemical stain, and the results are shown in FIG. 2 below.

As a result, in the case of the cosmetic composition (Example 12) containing Example 1, it could be confirmed that involucrin is expressed by being dyed with dark brown in all layers, except for the outermost part of the stratum corneum in the upper part of the basal cell layer in normal epidermis. The effect on the cosmetic composition (Example 12) containing Example 1 described above corresponds to a significant increase in the expression of involucrin which is a differentiation indicator protein, in artificial skin compared to the negative control group containing no compound of Examples and Comparative Example 1.

In brief, a pseudoceramide compound according to the present invention may exhibit an excellent effect on the differentiation of keratinocytes of the skin, and helps to form a stable and regular arrangement of the epidermal layer of the skin in orderly and dense layers. Therefore, the uniformity and firmness of the intercorneocyte lipids are improved, which is not only effective for enhancing a skin barrier function, but also easy to control the natural moisturizing factor, thereby exhibiting a high skin moisturizing effect.

A pseudoceramide compounds according to the present invention have a structure similar to that of natural ceramide to improve the uniformity and firmness of intercorneocyte lipids, which is not only effective for enhancing a skin barrier function, but also easy to control the natural moisturizing factor, thereby exhibiting a high skin moisturizing effect.

In addition, the effect of improving moisturizing ability, improving skin dryness, improving atopic dermatitis, improving itching, etc., may be exerted by applying a composition containing a pseudoceramide compound or a pharmaceutically acceptable salt or solvate thereof according to the present invention as an active ingredient in drugs or cosmetics.

Hereinabove, although the present invention has been described by specific matters and the limited embodiments, they have been provided only for assisting in a more general understanding of the present invention. Therefore, the present invention is not limited to the exemplary embodiments. Various modifications and changes may be made by those skilled in the art to which the present invention pertains from this description.

Therefore, the spirit of the present invention should not be limited to the above-mentioned embodiments, but the claims and all of the modifications equal or equivalent to the claims are intended to fall within the scope and spirit of the present invention.

What is claimed is:

1. A pseudoceramide compound represented by the following Formula 1:

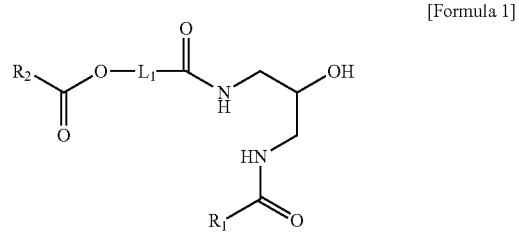

[Formula 1]

wherein $R_1$ is (C1-C30) alkyl, (C2-C30) alkenyl, or (C2-C30) alkynyl;

$R_2$ is (C1-C30) alkyl or (C2-C30) alkenyl; and $L_1$ is (C1-C30) alkylene, (C2-C30) alkenylene, or (C2-C30) alkynylene;

or a pharmaceutically acceptable salt or solvate thereof.

2. The pseudoceramide compound of claim 1, wherein in Formula 1, $R_1$ is (C1-C30) alkyl or (C2-C30) alkenyl, $R_2$ is linear (C1-C30) alkyl, and $L_1$ is (C2-C30) alkylene; or a pharmaceutically acceptable salt or solvate thereof.

3. The pseudoceramide compound of claim 1, wherein in Formula 1, $R_1$ is (C7-C30) alkyl or (C7-C30) alkenyl, $R_2$ is linear (C7-C30) alkyl, and $L_1$ is (C7-C30) alkylene; or a pharmaceutically acceptable salt or solvate thereof.

4. The pseudoceramide compound of claim 1, wherein the pseudoceramide compound is selected from the following structures:

1

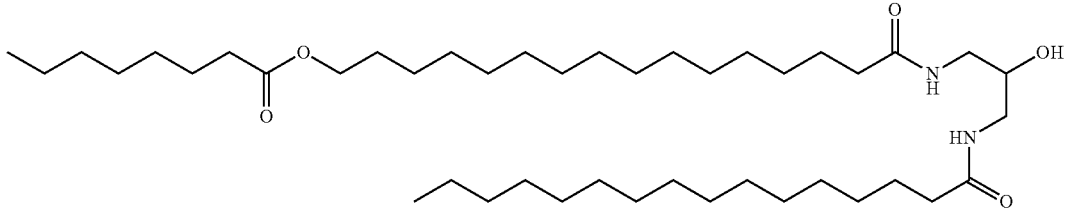

-continued
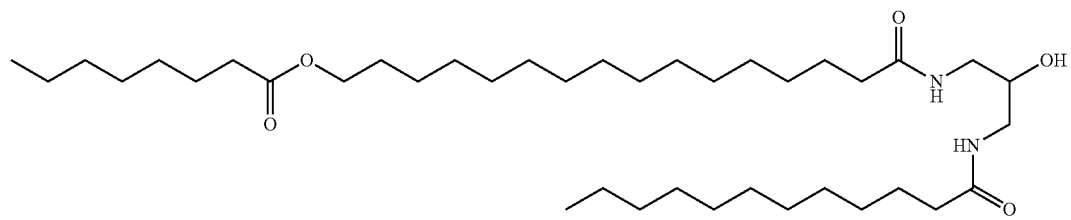
2
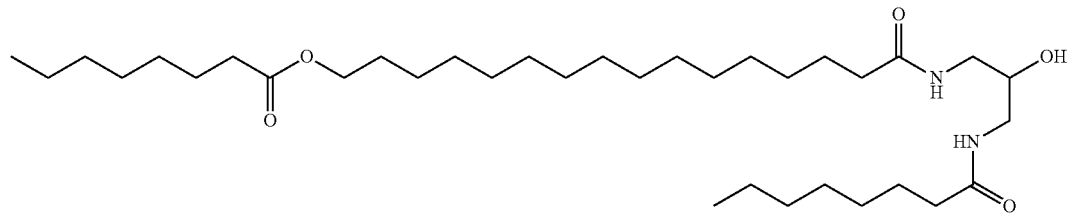
3
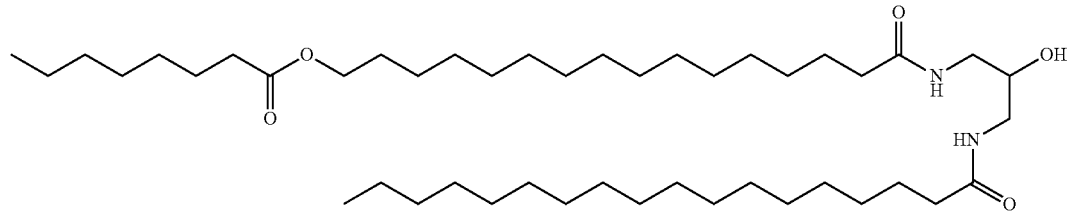
4
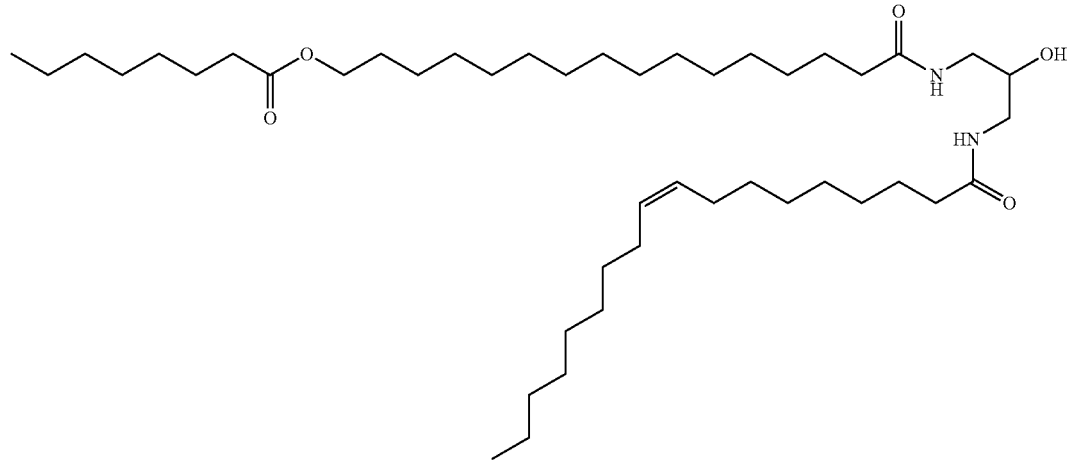
5
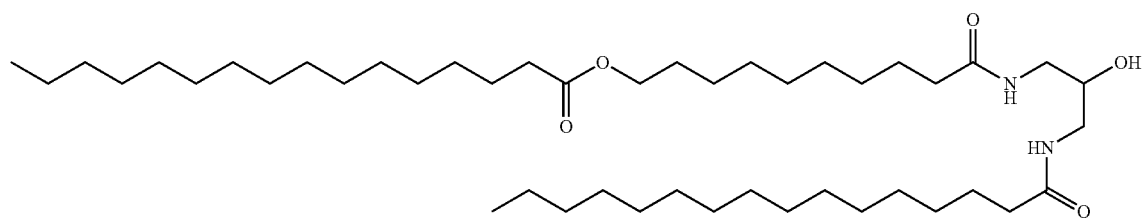
6
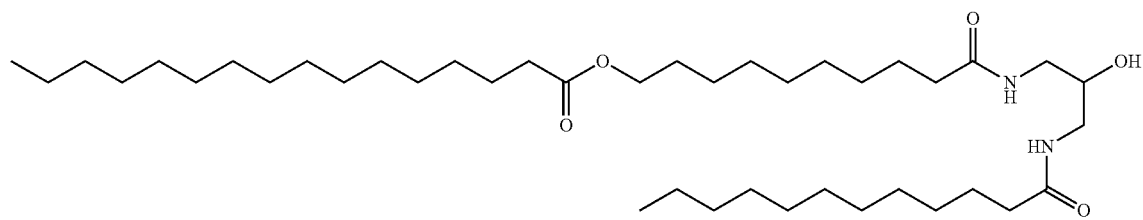
7

-continued

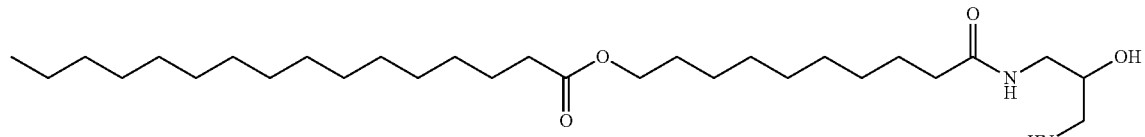
8

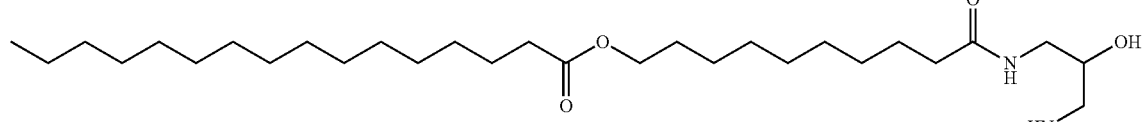
9

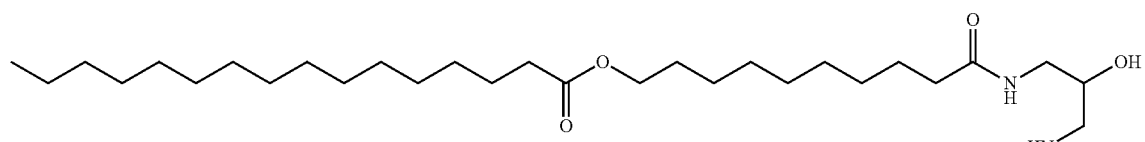
10

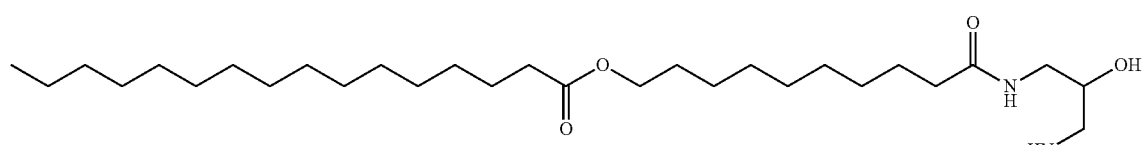
11

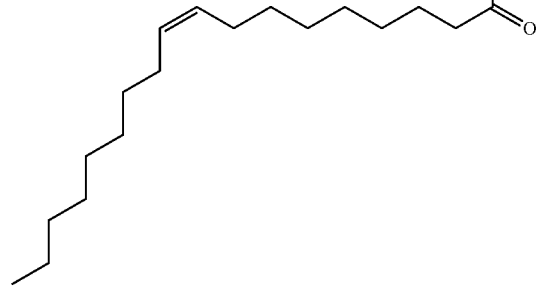

or a pharmaceutically acceptable salt or solvate thereof.

5. A pharmaceutical composition for improving a skin barrier function and improving inflammatory skin disease, comprising a pseudoceramide compound represented by the following Formula 1:

[Formula 1]

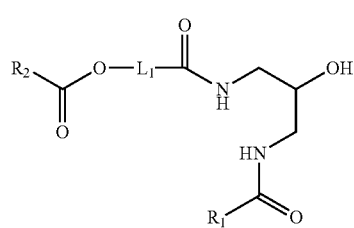

wherein $R_1$ is (C1-C30) alkyl, (C2-C30) alkenyl, or (C2-C30) alkynyl;

$R_2$ is (C1-C30) alkyl or (C2-C30) alkenyl; and $L_1$ is (C1-C30) alkylene, (C2-C30) alkenylene, or (C2-C30) alkynylene;

or a pharmaceutically acceptable salt or solvate thereof as an active ingredient.

6. The pharmaceutical composition of claim 5, wherein the inflammatory skin disease is atopic dermatitis, psoriasis, contact dermatitis, eczema dermatitis, photodermatitis, seborrheic dermatitis, herpes dermatitis, lichen planus, lichen sclerosus, pyoderma gangrenosum, pemphigus, epidermolysis bullosa, or systemic sclerosis.

7. The pharmaceutical composition of claim 5, wherein the pharmaceutical composition comprises an active ingredient in an amount of 0.001 to 20 wt %, based on the total weight of the composition.

8. A cosmetic composition for improving a skin barrier function and enhancing skin moisture, comprising a pseudo-ceramide compound represented by the following Formula 1:

[Formula 1]

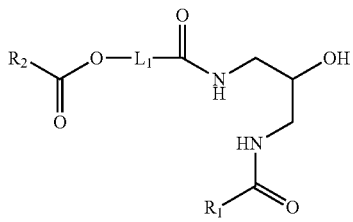

wherein $R_1$ is (C1-C30) alkyl, (C2-C30) alkenyl, or (C2-C30) alkynyl;

$R_2$ is (C1-C30) alkyl or (C2-C30) alkenyl; and $L_1$ is (C1-C30) alkylene, (C2-C30) alkenylene, or (C2-C30) alkynylene;

or a pharmaceutically acceptable salt or solvate thereof as an active ingredient.

9. The cosmetic composition of claim 8, further comprising intercorneocyte lipids or lipid complexes similar thereto.

10. The cosmetic composition of claim 9, wherein the intercorneocyte lipids or lipid complexes similar thereto are one or more selected from cholesterol, phytosterol, sphingosine, phytosphingosine, and cerebroside; ceramide I; ceramide II; ceramide III; ceramide IIIB; ceramide IV; ceramide V; and ceramide VI, myristoyl/palmitoyl oxostearamide/arachamide MEA, and dihydroxyisopropyl palmoyl palmamide.

11. The cosmetic composition of claim 8, wherein the cosmetic composition comprises an active ingredient in an amount of 0.001 to 20 wt %, based on the total weight of the composition.

* * * * *